United States Patent [19]

Schapira et al.

[11] Patent Number: 4,813,999

[45] Date of Patent: Mar. 21, 1989

[54] HERBICIDAL PRODUCTS BASED ON BROMOXYNIL AND/OR IOXYNIL ESTERS

[75] Inventors: Joseph Schapira, Paris; Jacques Pecheur, Courbevoie; Jacques Vincent, Mareil Marly; Patrick Droniou, Colombes; Jean-Paul Fournials, Cergy, all of France

[73] Assignee: Compagnie Francaise de Produits Industriels, Gennevilliers, France

[21] Appl. No.: 939,802

[22] Filed: Dec. 9, 1986

[30] Foreign Application Priority Data

Dec. 9, 1985 [FR] France ................. 85 18225

[51] Int. Cl.$^4$ ........................... A01N 37/34
[52] U.S. Cl. ........................... 71/105; 71/93; 71/108; 71/109; 71/116; 71/DIG. 1
[58] Field of Search ............ 71/105, DIG. 1

[56] References Cited

U.S. PATENT DOCUMENTS

| | | | |
|---|---|---|---|
| 3,592,626 | 7/1971 | Heywood et al. | 71/105 |
| 4,332,613 | 6/1982 | Esposito | 71/105 |
| 4,349,488 | 9/1982 | Dentel et al. | 558/414 |

FOREIGN PATENT DOCUMENTS

| | | | |
|---|---|---|---|
| 0031684 | 7/1981 | European Pat. Off. | 71/105 |
| 2556933 | 6/1985 | France | 71/105 |
| 432120 | 9/1967 | Switzerland | 71/105 |
| 2152376 | 12/1983 | United Kingdom | 71/105 |

OTHER PUBLICATIONS

Chem. Abst., vol. 102 (1985), 175027r, Denko-Benzonitrile in Secondary Battery.
Chem. Abst., vol. 99 (1983), 176441c Klosiewicz-Benzonitrile Catalyst in Polymer Production.
Chem. Abst., vol. 101 (1984) 121600h, AMP, Inc.-Benzonitrile Used in Inks in Printed Circuitry.

*Primary Examiner*—Glennon H. Hollrah
*Assistant Examiner*—S. Treanor
*Attorney, Agent, or Firm*—Fleit, Jacobson, Cohn & Price

[57] ABSTRACT

Herbicidal products comprising a mixture of one or several linear acid esters and one or several branched acid esters of bromoxynil and/or a mixture of one or several linear acid esters and one or several branched acid esters of ioxynil, the proportion of linear acid esters of bromoxynil in the mixture of the latter with the branched acid esters of bromoxynil being from 20-90%, preferably from 30-80% molar and the proportion of linear acid esters of ioxynil in the mixture of the latter with the branched acid esters of ioxynil being from 30-95% and, preferably, from 40-85% molar, with the proportion of branched acid esters representing each time the complement to 100%.

16 Claims, 1 Drawing Sheet

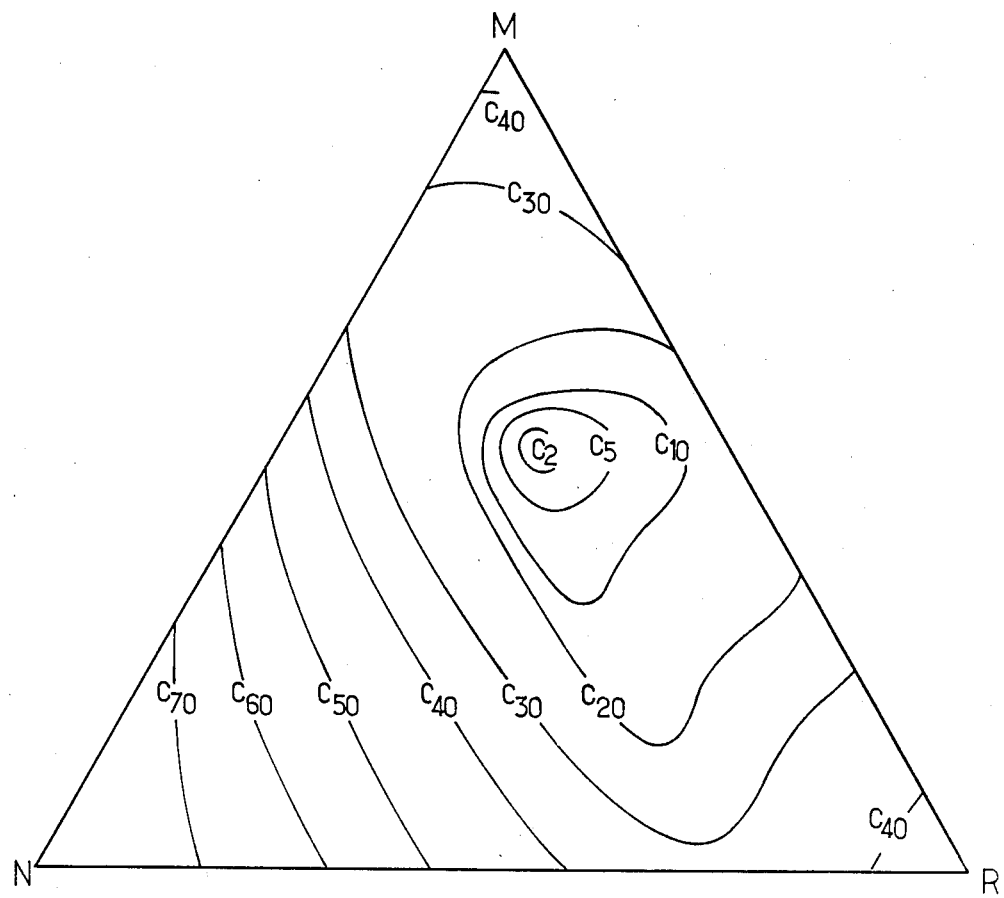

HERBICIDAL PRODUCTS BASED ON BROMOXYNIL AND/OR IOXYNIL ESTERS

BACKGROUND OF THE INVENTION

The invention relates to herbicidal products based on esters of bromoxynil and/or ioxynil.

Herbicidal products of the type concerned comprise, as active substance, mixtures of bromoxynil and/or ioxynil esters and are in the form of solutions of these esters in solvents, advantageously in the presence of surface-active substances adapted to render them dispersible in water for their application by spraying.

These solutions of bromoxynil and/or ioxynil esters in solvents comprising surface-active products are denoted by the term "emulsifiable concentrates".

Herbicidal products of the type concerned are already known which are based on 3.5-dibromo-4-hydroxybenzonitrile n-octanoate (or bromoxynil n-octanoate) and/or 3.5-diiodo-4-hydroxy-benzontirile n-octanoate (or ioxynil n-octanoate); the principal use of these products resides in the destruction of dicotyledon adventitious species in the post-spearing or sprouting phase of cereal cultivation; it is recalled moreover that bromoxynil n-octanoate is a waxy, cream colored solid of melting point 45°–46° C. when it is pure and 36°–40° C. when it is of technical quality and that ioxynil n-octanoate is a waxy solid of cream to brown colour, of melting point 59°–60° C. when it is pure and 50°–55° C. when it is of technical quality.

These herbicidal products have the drawback, for reasons of behaviour at low temperature, of not permitting concentrations, for products of commercial quality, higher than 240 g of bromoxynil or ioxynil equivalent per liter since, at the latter concentration, the corresponding solutions of bromoxynil or ioxynil n-octanoate crystallize at −7° C. and, for example, at 480 g/l, the crystallization starts from 20° C.

Now, the crystallization temperature of solutions or of emulsifiable concentrates of bromoxynil or ioxynil esters is a limiting factor for the concentration of these products since, on the one hand, these products are often manufactured and stored in winter and, on the other hand, the crystalline product is very difficult to reliquefy and it remains in any case heterogeneous and hence unsuitable for any subsequent use.

To overcome this drawback, it has already been proposed, in the case of herbicidal substances of the type concerned which are based on bromoxynil n-octanoate (French Pat. No. 84 19489) to incorporate with said products a substantial proportion of bromoxynil heptanoate, due to which it becomes possible to provide products containing up to 500 g/l of bromoxynil equivalent without crystallizing at −7° C. for herbicidal properties very similar to those of the products based on n-octanoate alone.

It has also been proposed (U.S. Pat. No. 4,332,613) to incorporate with said herbicidal products a substantial proportion of bromoxynil and/or ioxynil n-butyrate. Here again, the crystallization point is lowered to a value below −7° C. for concentrations which can reach 600 g/l of bromoxynil and/or ioxynil equivalent. Concentrations ranging up to 800 g/l are provided but not preferred since they do not ensure an absence of crystallization at −7° C.

Applicants have made it their particular objective, to do better and to provide herbicidal products of the type concerned which, for concentrations of a bromoxynil and/or ioxynil equivalent higher than those of the prior art, have a freezing point lower than, and at the most equal to, that of known products.

And they have found that this objective could be achieved through herbicidal substances of the type concerned comprising in solution, in solvents and preferably in the presence of surface-active products, admixtures of straight and branched acid esters of bromoxynil and/or ioxynil.

These products show, surprisingly and unexpectedly, cold behaviour characteristics improved with respect to those of products formed from bromoxynil and/or ioxynil octanoate alone or in admixture with the other linear acid esters described in the above-identified patents.

And still more surprisingly and unexpectedly, these products formed according to the invention show phytoactivities equivalent to those of the prior art products despite the well-known fact (see for example the article of B. J. Heywood which appeared under the title "Hydroxybenzonitrile Herbicides" in the issue of 19 Nov. 1966 of the review "Chemistry and Industry") that the branched acid esters of bromoxynil and ioxynil show very low phytoactivity, and even practically nil.

GENERAL DESCRIPTION OF THE INVENTION

Consequently, the herbicidal products according to the invention comprise in solution in solvents and preferably in the presence of surface-active agents, a mixture of one or several linear acid esters and one or several branched acid esters of bromoxynil and/or a mixture of one or several linear acid esters and one or several branched acid esters of ioxynil, the proportion of linear acid esters of bromoxynil in the mixture of the latter with the branched acid esters of bromoxynil being from 20–90%, preferably from 30–80% molar and the proportion of linear acid esters of ioxynil in the mixture of the latter with the branched acid esters of ioxynil being from 30–95% and, preferably, from 40–85% molar, with the proportion of branched acid esters representing each time the complement to 100%.

The invention is aimed, of course, besides the above-said herbicidal products, at mixtures of linear acid esters and of branched acid esters of bromoxynil and of ioxynil proper and which constitute thereof the active material and which show melting points distinctly below those of the n-octanoate, equimolecular mixtures n-octanoate/n-butyrate and n-octanoate/n-heptanoate and components of the various esters constituting the mixtures.

It is aimed, in addition, at spraying fluids applied to the soil and which are obtained from the above-said herbicidal products according to the invention by dilution or emulsion in water; it is directed lastly at a process for destroying adventitious species by the application of the herbicidal products according to the invention.

In the above-said mixtures of linear and branched esters, is meant by linear acids, aliphatic acids comprising a linear hydrocarbon chain composed of 3–9 carbon atoms, namely n-propionic, n-butyric, n-valeric, n-caproic, n-heptanoic, n-octanoic and n-nonanoic acids, by branched acids, aliphatic acids comprising a principal hydrocarbon chain composed of 3–8 carbon atoms and 1–3 side chains comprising in total between 1 and 3 carbon atoms, namely particularly the 2-methylpropanoic, 2.2-dimethyl-propanoic, 2-methyl-butyric, 3-methyl-butyric, 2-ethyl-butyric, 2.2-dimethyl-butyric, 2-ethyl-2-methyl-butyric, 2-methyl-pentanoic, 2-n-propyl-pentanoic, 2-methyl-hexanoic, 2-ethyl-hexanoic acids and mixtures containing these acids such as, for example, that which is denoted by the name cekanoic acid CK 7 (CDF Company), that which is denoted by the name isooctanoic acid (HOECHST Company) and that which is denoted by the expression isononanoic (SNPE Company).

To fix ideas, it is indicated that the above-said cekanoic acid is marketed by the CDF Chimie Company under the name cekanoic acid CK 7; it is obtained by synthesis and its composition is as follows:
Content of $C_7$ acids 98.5% minimum
Content of n-heptanoic acid 10±2%
Content of branched $C_7$ acids 89±2%
Distribution of the isomers:
2-methyl-pentanoic acid 15 to 20%
2-methyl-hexanoic acid 60 to 70%
other methyl hexanoic isomers 5 to 10%.

The esters of cekanoic acid CK 7 are below called cekanoates.

To prepare the above-said mixtures of esters, it is possible either to mix in the liquid state and hot the various esters previously synthesized, or to esterify the ioxynil and/or the bromoxynil successively or simultaneously by means of various esterifying agents, namely the chlorides or anhydrides of the acids concerned.

The anhydrides and chlorides of all the acids mentioned are industrial and the esterifications can be performed without particular difficulty by the man skilled in the art.

The herbicidal products according to the invention are distinguished by concentrations of ioxynil and bromoxynil equivalents stronger than it was possible to achieve hitherto, whilst showing remarkable cold behaviour manifested by the absence of crystallization after a week of storage at 0° C.; these concentrations are 100–900 g of bromoxynil equivalent and 100–1100 g of ioxynil equivalent per liter.

In practice, the concentration in bromoxynil and/or ioxynil equivalent is higher than about 600 g/l and does not exceed about 900 g/l.

Another advantage of the herbicidal products according to the invention resides in the reduction of the production cost of the formulations of bromoxynil and/or ioxynil esters by, on the one hand, lower cost of heating the esters, during the manufacture of the formulation, due to the fact of the low melting point of the mixture of esters and, on the other hand, a lower cost of raw material to the extent that, for a part, branched acids which are cheap, are used.

Another advantage resides in the fact that the formulation which can be more concentrated in active material use, consequently, less inert ingredients, responsible for costs, necessitate less packaging to treat a given area and hence reduce the cost of packaging, of shipping and of storage, as well as the problems of elimination of worn packages.

The herbicidal products according to the invention may also contain other herbicides having a good solubility in hydrocarbons like, for example, derivatives of the family of biphenylethers among which are Bifenox (methyl-2.4-dichloro-phenoxy-2-nitrobenzoate), the derivatives of benzoic acid among which are Dicamba (3.6-dichloro-2-methoxy-benzoic acid), the derivatives of picolinic acid among which are 3.6-dichloro-piolinic acid, the derivatives of triazines among which are cyanazine (4-chloro-6-ethylamino-1.3.5-triazin-2-yl-amino)-2-methyl-propionitrile), the esters of isooctanol or of butylglycol of (2.4-dichloro-phenoxy)-acetic acid, of (4-chloro-2-methylphenoxy)-acetic acid, of (±) 2-(4-chloro-2-methyl-phenoxy)-propionic acid or of (±) 2-(2.4-dichloro-phenoxy)-propionic acid.

The amount of these other herbicides in these liquid herbicidal products depends on their herbicidal effectiveness.

By convention, in the following, all the proportions between esters are expressed in molar percentages of the esters.

For example, for a given composition, it is equivalent to writing that a formulation titrates at 900 g/l of bromoxynil in the following molar proportions of esters:
bromoxynil n-heptanoate: 50%
bromoxynil n-butyrate: 20%
bromoxynil 2-ethyl-hexanoate: 30%
or to write this formulation titrates:
450 g/l of bromoxynil in the form of n-heptanoic ester
180 g/l of bromoxynil in the form of n-butyric ester
270 g/l of bromoxynil in the form of 2-ethyl-hexanoic ester.

The herbicidal products according to the invention are liquid products dilutable with water to give spraying fluids suitable for application on plants; they comprise, besides the mixtures of bromoxynil and/or ioxynil esters defined above, one or several solvents and ionic or non-ionic surface-active agents.

As solvents, there will be employed petroleum hydrocarbons, particularly aromatic and paraffin fractions; other solvents other than petroleum solvents, such as animal, vegetable and synthetic oils can also be employed.

Preferably, mineral oils with a high content of aromatic products and more particularly those having a content by weight of aromatic products of at least 70% and a flash point higher than 50° C. are used. A preferred solvent is that marketed by EXXON under the mark SOLVESSO 200 and which contains 99% of aromatic products. Alcohols having a straight, branched or cyclic hydrocarbon chain, composed of at least 6 carbon atoms, polyol compounds like for example ethyleneglycol, butylglycol or those marketed under the mark DOWANOL by the DOW Company, can also be used.

As surface-active agents, there may be used, sulforicinoleates, quaternary ammonium derivatives, products based on ethylene oxide condensates with propylene oxide or with alkylphenols, for example nonyl or octyl, or polyarylphenols, or with saponified or not vegetable oils or again with straight or branched alcohols, for example lauric alcohol. It is also possible to use carboxylic esters of anhydrosorbitols possibly polyethoxylated, alkali salts, alkaline-earth or ammonium sulphuric esters, sulfonic derivatives of high molecular weight, such as lignosulphonates or alkylbenzene-sulphonates of sodium and of calcium. Lastly it is also possible to use alkali, alkaline-earth, ammonium or amine salts of carboxylic acids.

These surface-active agents are used preferably in the proportion of 0.1 to 20% by weight/weight, either in hydrocarbons like, for example, a mineral oil having a flash point higher than 50° C. and a content by weight of aromatic products of at least 70%, or in short alcohols like methanol, isopropanol or isobutanol.

The spraying fluids obtained by dilution with water of the herbicidal products according to the invention contain from 0.05 to 5% in weight/volume of a mixture of straight and branched esters of bromoxynil and/or ioxynil and are used in the method of destroying adventitious species, according to the invention, at herbicidal application doses of 50 g to 1 kg per hectare of bromoxynil and/or ioxynil equivalents.

DESCRIPTION OF PREFERRED EMBODIMENTS

In the following, there is first of all established, by means of experiments I, II and III, the advantageously low melting points of the mixtures of linear or branched bromoxynil or ioxynil esters constituting the active material of the herbicidal products according to the invention and which are manifested by the good behaviour to cold of the latter and then there are illustrated by Examples 1 to 9 a certain number of herbicidal products constituting advantageous embodiments of the invention.

EXPERIMENT I

The bromoxynil esters and ester mixtures identified in Table A under numbers 1 to 15, are prepared by mixing, as the case may require, suitable amounts of the various esters. Each ester or ester mixture is then melted and the melted mass is stirred to render it homogeneous. It is then cooled rapidly to −10° C. by external cooling. A specimen of crystals of the frozen solid mass thus obtained is placed in a capillary tube which is then placed in a Thiele tube forming a water bath (ref. Prolabo, capillary: 09 224 914; Thiele tube: 09 058 156). The Thiele tube enables stirring by thermo-siphon. The temperature of the water bath is gently raised and the temperature at which a meniscus appears for the first time, as the melting point of the mixture concerned, is recorded.

The mixtures of linear and branched acid esters are optimised and there is noted for each mixture the molar composition ensuring the lowest melting point for the constituents concerned. This temperature is indicated in Table A.

TABLE A

| N' of ester or ester mixture | Nature of esters | % molar in the mixture | Melting point (°C.) |
|---|---|---|---|
| 1 | bromoxynil n-octanoate | 100 | 37 |
| 2 | bromoxynil n-heptanoate | 100 | 45 |
| 3 | bromoxynil n-butyrate | 100 | 82 |
| 4 | bromoxynil 2-ethyl-hexanoate | 100 | 43 |
| 5 | bromoxynil cekanoate | 100 | 27 |
| 6 | bromoxynil n-octanoate | 50 | 24 |
|   | bromoxynil n-butyrate | 50 | |
| 7 | bromoxynil n-octanoate | 50 | 26 |
|   | bromoxynil n-heptanoate | 50 | |
| 8 | bromoxynil n-heptanoate | 50 | 14 |
|   | bromoxynil 2-ethyl-hexanoate | 50 | |
| 9 | bromoxynil n-heptanoate | 50 | 9 |
|   | bromoxynil cekanoate | 50 | |
| 10 | bromoxynil n-octanoate | 50 | 7 |
|   | bromoxynil 2-ethyl-hexanoate | 50 | |
| 11 | bromoxynil n-octanoate | 40 | 5 |
|   | bromoxynil n-heptanoate | 20 | |
|   | bromoxynil 2-ethyl-hexanoate | 40 | |
|   | bromoxynil n-octanoate | 40 | |
| 12 | bromoxynil n-butyrate | 20 | 5 |
|   | bromoxynil 2-ethyl hexanoate | 40 | |
|   | bromoxynil n-octanoate | 20 | |
| 13 | bromoxynil n-butyrate | 20 | 5 |
|   | bromoxynil cekanoate | 60 | |
|   | bromoxynil n-heptanoate | 50 | |
| 14 | bromoxynil n-butyrate | 20 | 2 |
|   | bromoxynil 2-ethyl-hexanoate | 30 | |
|   | bromoxynil n-heptanoate | 40 | |
| 15 | bromoxynil n-butyrate | 20 | 2 |
|   | bromoxynil cekanoate | 40 | |

The mixtures 8 to 15, which all comprise a certain proportion, adjusted optimally for each, of branched acid esters of bromoxynil, possess a lower melting point than the esters and mixtures of esters 1 to 7 which comprise particularly the constituents of the mixtures 8 to 15 taken separately.

EXPERIMENT II

In order to explain better the manner adopted to define the optimised compositions retained, the diagram shown in the FIGURE is constructed which permits the determination of the area of the mixtures "bromoxynil n-heptanoate/bromoxynil n-butyrate/bromoxynil 2-ethylhexanoate" which show the lowest melting point.

The diagram of the FIGURE is in the form of an equilateral triangle whose apices M, N, R show respectively each of the constituents of the mixture, namely bromoxynil n-heptanoate (melting point 45° C.), bromoxynil n-butyrate (melting point 82° C.) and bromoxynil 2-ethyl-hexanoate (melting point 43° C.), whose sides MN, NR and RM show respectively all the binary mixtures obtained from the products represented by the apices "M and N", "N and R" and "R and M", and of which each of the points P within the area of the triangle represents a ternary mixture whose molar composition of each of the three constituents is obtained by passing through P a parallel to each of the sides of the triangle up to the intersection with the two other sides, which provides the molar proportion of the constituent represented by the apex opposite the side with respect to which the parallel has been drawn.

Procedure is as for Experiment I by mixing weighed amount of each of the three esters and sufficient mixtures are formed to cross rule the area of the triangle and for each of these points, that is to say for each of the mixtures, the melting point is determined in the same manner as in Experiment I; to form the sides of the triangle, a certain number of binary mixtures are made of which the melting points are also determined.

Finally the points representing the mixtures of the same melting point are joined up, which provides a certain number of curves C70, C60 . . . C2 which give the composition of all the mixtures which, for the first, melt at 70° C. and so on.

In the present case, it is the mixtures represented by the curve C2 which have the lowest melting point, namely 2° C.

EXPERIMENT III

The ioxynil esters and ester mixtures identified in Table B under numbers 16 to 24, are prepared in the same manner as in Experiment I, as the case may require, by mixing.

The melting points are also measured, according to the same principle as in Experiment I, and for each mixture the molar composition ensuring the lowest melting point for the constituents concerned is noted.

TABLE B

| N' of ester or ester mixture | Nature of esters | % molar in the mixture | Melting point (°C.) |
|---|---|---|---|
| 16 | ioxynil n-octanoate | 100 | 50 |
| 17 | ioxynil n-heptanoate | 100 | 68 |
| 18 | ioxynil n-butyrate | 100 | 118 |
| 19 | ioxynil 2-ethyl-hexanoate | 100 | 66 |
| 20 | ioxynil cekanoate | 100 | 61 |
| 21 | ioxynil n-octanoate | 67 | 38 |
|    | ioxynil n-butyrate | 33 |    |
| 22 | ioxynil n-octanoate | 50 | 33 |
|    | ioxynil 2-ethyl-hexanoate | 50 |    |
| 23 | ioxynil n-octanoate | 30 | 31 |
|    | ioxynil n-butyrate | 20 |    |
|    | ioxynil cekanoate | 50 |    |
| 24 | ioxynil n-heptanoate | 37 | 35 |
|    | ioxynil n-butyrate | 18 |    |
|    | ioxynil cekanoate | 45 |    |

Here again, the mixtures 22, 23 and 24 which all include a certain proportion, adjusted in optimum manner for each, of branched acid esters of ioxynil, possess a lower melting point than the esters or mixtures 16 and 21 which comprise particularly their constituents taken separately.

The following are the Examples considered above.

EXAMPLE 1

Five solvent solutions a, b, c, d and e usable as emulsifiable concentrates and containing 750 g/l of bromoxynil equivalent are prepared by dissolving different bromoxynil esters in a mineral oil essentially aromatic constituted by that known under the trademark SOLVESSO 200.

These solutions are shaken until homogeneity and a clear liquid appearance. To these solutions is added a mixture of anionic and non-ionic emulsifying agents marketed by Applicants under the trademark GALORYL EM 458 in the proportion of 7% (weight/weight) of GALORYL EM 458 with respect to the solution.

The proportions of the various esters entering into the constitution of each of the solutions a to e are indicated in Table C and expressed in molar percentages. The behaviour of each solution at different cold storage temperatures after seeding the solutions with tiny amounts of the solid ester mixture associated with each of them, is observed.

TABLE C

| | Solution n' (in molar percentages) | | | | |
|---|---|---|---|---|---|
| | a | b | c | d | e |
| bromoxynil n-octanoate | 50 | 50 | | | |
| bromoxynil n-heptanoate | | 50 | 67 | 50 | 40 |
| bromoxynil n-butyrate | 50 | | 33 | 25 | 20 |
| bromoxynil 2-ethyl-hexanoate | | | | 25 | |
| bromoxynil cekanoate | | | | | 40 |
| Density of the solution at 20° C. | 1.380 | 1.367 | 1.396 | 1.367 | 1.370 |
| Appearance at 0° C. | crystalline | crystalline | crystalline | liquid | liquid |
| Appearance at −8° C. | idem | idem | idem | idem | idem |
| Appearance at −13° C. | idem | idem | idem | idem | idem |
| Appearance at −18° C. | idem | idem | idem | idem | idem |

It is concluded from this table that the only solutions showing an industrially acceptable cold behaviour are those according to the invention, namely the solutions d and e.

EXAMPLE 2

In the same way as in Example 1, five solutions f to k containing 750 g/l of ioxynil equivalent produced by mixing various ioxynil esters in the solvent SOLVESSO 200, were prepared. To these solutions shaken and rendered homogeneous and of clear appearance, was added as surface-active agent GALORYL EM 458 in the same proportion as in Example 1.

The proportions of the various esters each constituting solutions are indicated in Table D, again expressed as molar percentages.

The cold behaviour is again observed, after seeding carried out with tiny amounts of the solid mixture of esters adapted to each solution.

TABLE D

| | Solution n' (in molar percentages) | | | | |
|---|---|---|---|---|---|
| | f | g | h | i | k |
| ioxynil n-octanoate | 67 | 33 | | | |
| ioxynil n-heptanoate | | 67 | 67 | 50 | 35 |
| ioxynil n-butyrate | 33 | | 33 | 20 | 15 |
| ioxynil 2-ethyl-hexanoate | | | | 30 | |
| ioxynil cekanoate | | | | | 50 |
| Density of the solution at 20° C. | 1.457 | 1.465 | 1.471 | 1.447 | 1.440 |
| Appearance at 0° C. | crystalline | crys-* talline | crystalline | liquid | liquid |
| Appearance at −8° C. | idem | idem | idem | idem | idem |
| Appearance at −13° C. | idem | idem | idem | crystalline ** | crystalline ** |

*spontaneous crystallization before any seeding
**crystallization after 15 days only of storage at this temperature It results from this Table that the only solutions showing an industrially acceptable cold behaviour are those according to the invention (solutions i and k).

EXAMPLE 3

In the same way as in Examples 1 and 2, a solution containing 900 g/l of bromoxynil equivalent produced by mixing bromoxynil n-heptanoate, n-butyrate and 2-ethyl-hexanoate in the respective molar percentages 50/25/25 and in the solvent SOLVESSO 200 were prepared. As surface-active agent, there is added, GALORYL EM 458 in the proportion of 7% (weight/weight) with respect to the final solution. This formulation has a density at 20° C. of 1.443. Its temperature is brought to 0° C., then it is seeded with an tiny amount of the mixture of esters composing it, the latter having been previously cooled until it sets. Under these conditions, it must stay about one month in storage before an appreciable start of crystallization around the seeds introduced at the start.

The same formulation placed at −8° C. crystallizes, after seeding, in about 3-4 days.

The formulation of Example 3 is usable for temperate climates whose temperature does not drop for long periods below 0° C.

It is to be noted that it is constituted, as mentioned in Experiment I, by a mixture of esters whose melting point is about 2° C. No crystallization is hence to be feared above this temperature.

EXAMPLE 4

In the same way as in Examples 1 to 3, three emulsifiable concentrates l, m and $p_2$ containing respectively 600 g/l of bromoxynil equivalent in the form, for the first, of a mixture of bromoxynil n-heptanoate, n-butyrate and 2-ethyl-hexanoate, for the second, of a mixture of bromoxynil n-heptanoate, n-butyrate and cekanoate and, for the third, of a mixture of bromoxynil n-octanoate, n-butyrate and 2-ethyl-hexanoate were prepared.

Also two emulsifiable concentrates n and $p_1$ containing 600 g/l of ioxynil equivalent in the form, for the first, of a mixture of ioxynil n-heptanoate, n-butyrate and 2-ethyl-hexanoate and, for the second, of a mixture of ioxynil n-heptanoate, n-butyrate and cekanoate were prepared.

The five emulsifiable concentrates comprise, apart from the ester mixtures, a solvent, namely SOLVESSO 200 and adjusted mixtures of anionic and non-ionic emulsifiers, among which were GALORYL EM 4039 which is a mixture of anionic and non-ionic emulsifiers marketed by Applicants.

The molar proportions of the esters composing the abovesaid products are indicated in Table E in molar percentages and the proportions of the emulsifiers enabling a dilute aqueous emulsion stable at least two hours are indicated in percentages by weight with respect to the emulsifiable concentrate.

TABLE E

| | l | m | n | $p_1$ | $p_2$ |
|---|---|---|---|---|---|
| Proportions of oxynil esters | | | | | |
| bromoxynil n-octanoate | | | | | 40 |
| bromoxynil n-heptanoate | 50 | | 40 | | |
| ioxynil n-heptanoate | | 50 | | 35 | |
| bromoxynil n-butyrate | 25 | | 20 | | 20 |
| ioxynil n-butyrate | | 20 | | 15 | |
| bromoxynil 2-ethyl-hexanoate | 25 | | | | 40 |
| ioxynil 2-ethyl-hexanoate | | 30 | | | |
| bromoxynil cekanoate | | | 40 | | |
| ioxynil cekanoate | | | | 50 | |
| Proportions of emulsifiers in the emulsifiable concentrate | | | | | |
| CGALORYL EM 4039 | 4.60 | 7.1 | 4.15 | 7.5 | |
| Condensate of 20 moles OE in castor oil | 7.40 | 5.3 | 7.85 | 5.0 | |
| Condensate of 10 moles OE in castor oil | — | 2.6 | — | 2.5 | |
| Solvent: qsp 100% (w/w) | SOLVESSO 200 | | | | |
| Density of the emulsifiable concentrate at 20° C. | 1.298 | 1.374 | 1.301 | 1.364 | 1.295 |

The five emulsifiable concentrates thus prepared are homogeneous and liquid indefinitely when they are stored at a temperature of −18° C.

EXAMPLE 4 bis

In the same way as in Examples 1 to 4, two emulsifiable concentrates $p_3$ and $p_4$ containing 720 g/l of bromoxynil equivalent in the form, for the first, of a mixture of bromoxynil n-octanoate, n-butyrate and 2-ethyl-hexanoate and, for the second, of a mixture of bromoxynil n-heptanoate, n-butyrate and 2-ethyl-hexanoate were prepared.

The two emulsifiable concentrates comprise, apart from the ester mixtures, a solvent, namely SOLVESSO 200 and adjusted mixtures of anionic and non-ionic emulsifiers, among which were GALORYL EM 4036 and GALORYL EM 4039 which are mixtures of anionic and non-ionic emulsifiers marketed by Applicants.

The molar proportions of the esters composing the abovesaid products are indicated in Table E' in molar percentages and the proportions of the emulsifiers enabling a dilute aqueous emulsion stable at least two hours are indicated in percentages by weight with respect to the emulsifiable concentrate.

TABLE E'

| | $p_3$ | $p_4$ |
|---|---|---|
| Proportions of oxynils esters | | |
| bromoxynil n-octanoate | 40 | |
| bromoxynil n-heptanoate | | 50 |
| bromoxynil n-butyrate | 20 | 20 |
| bromoxynil 2-ethyl-hexanoate | 40 | 30 |
| Proportions of emulsifying agents in the emulsifiable concentrate | | |
| Galoryl EM 4036 | 9 | |
| Galoryl EM 4039 | | 4 |
| Condensate of 10 moles OE in castor oil | 11 | 9 |
| Solvent: qsp 100% (w/w) | SOLVESSO 200 | |
| Density of the emulsifiable concentrate at 20° C. | 1.361 | 1.358 |

The two emulsifiable concentrates thus prepared are homogeneous and liquid indefinitely when they are stored at a temperature of −3° C. for the formula $p_3$ and −8° C. for the formula $p_4$.

The phytoactivity of the herbicidal products according to the invention is illustrated by comparative tests carried out firstly in greenhouse, then in the fields.

In these tests, there were used as products of comparison the octanoic esters of ioxynil and/or bromoxynil which are selective herbicides, principally in cereal cultures with small seeds (wheat, barley, oats . . .) in Spring and the Fall, mais, sorghum, sugar cane and in other crops like onion, garlic and shallots, for the destruction of broad-leaf plants and principally dicotyledons.

Within the scope of the greenhouse tests, there were compared separately for ioxynil and for bromoxynil:
formulations according to the invention,
known formulations containing the n-octanoate and n-butyrate,
formulations containing only respectively one of the branched basic esters which enter into the composition of the abovesaid formulations according to the invention.

These tests show the absence of effectiveness of the formulae based only on branched esters of ioxynil and bromoxynil.

The conclusions which can be drawn from these trials are based on the percentage destruction of selected plants.

Within the scope of the field tests on cereals, the effectiveness of the formulations according to the invention with respect to formulations, on the one hand, based on octanoate and, on the other hand, based on octanoate-butyrate mixtures, was checked.

Hence the percentage destruction of adventitious flora as is found in each field was measured. Rather wide variations in values were obtained due to the fact that the dominant weeds are different from one field to another and occur during the treatment at a different vegetating stage. There were only taken into account results obtained on plants present in at least two fields to calculate the activities of the different mixtures.

For comparison purposes with the formulae according to the invention, mentioned in Example 4, Table E, there were formed emulsifiable concentrates in water from various bromoxynil or ioxynil esters; identification of these products results in Table F.

For all of the biological tests, the following marking was adopted:

| rating | behavior of the plant |
|---|---|
| 10 | Very sensitive, completely destroyed |
| ≧8 | Sensitive |
| ≧6 | Average sensitivity |
| ≧4 | Average sensitivity - average resistance |
| ≧2 | Average resistance |
| 0 | Resistant, none destroyed |

The comparative tests bear, both on the products based on bromoxynil and on those based on ioxynil,
- on two ester mixtures according to the invention appearing in Table E,
- or an ester mixture according to the prior art appearing in Table F,
- on a mixture of linear esters constituting a part of ester mixtures according to the invention, figuring in Table F and
- on two branched esters used alone and figuring also in Table F.

Two pots constituted controls and were not treated and each treatment was besides duplicated. The plants of each pot were observed 30 days after treatment and the ratings illustrating the state of the adventitious species were recorded and compared with the untreated control pots.

The results are given in Examples 5 (relating to products based on bromoxynil) and 5 (relating to products based on ioxynil).

The plants to which the experiments related were in the case of bromoxynil-based products:
*Amarantus retroflexus*
*Brassica oleifera*

TABLE F

| | Emulsifiable Concentrate no | | | | | | | | | |
|---|---|---|---|---|---|---|---|---|---|---|
| | q | r | s | t | u | v | w | x | y | z |
| Proportion in moles of oxynil esters (%) | | | | | | | | | | |
| bromoxynil n-octanoate | 50 | | | | | | | | 100 | 25 |
| ioxynil n-octanoate | | | | | 67 | | | | | 30 |
| bromoxynil n-heptanoate | | 50 | | | | | | | | |
| ioxynil n-heptanoate | | | | | | 67 | | | | |
| bromoxynil n-butyrate | 50 | 50 | | | | | | | | 25 |
| ioxynil n-butyrate | | | | | 33 | 33 | | | | 20 |
| bromoxynil cekanoate | | | 100 | | | | | | | |
| ioxynil cekanote | | | | | | | 100 | | | |
| bromoxynil 2-ethyl-hexanoate | | | | 100 | | | | | | |
| ioxynil 2-ethyl-hexanoate | | | | | | | | 100 | | |
| Content of active material in the emulsifiable concentrate (in g/l) | 480 bromo-xynil | 480 bromo-xynil | 240 bromo-xynil | 240 bromo-xynil | 480 Ioxy-nil | 480 Ioxy-nil | 240 Ioxy-nil | 240 Ioxy-nil | 240 Ioxy-nil | 480 (240 Ioxy-nil & 240 bromo-xynil) |
| Proportions of emulsifying agents in the emulsifiable concentrate (in %) | | | | | | | | | | |
| Galoryl EM 514 (*) | | 3.5 | | | | | | | | |
| Galoryl EM 4039 | 4.9 | | 4.5 | 4.5 | 4.8 | 5.5 | 4.3 | 4.4 | 4.6 | 5.5 |
| Condensate of 10 moles OE in castor oil | | | 1.5 | 1.5 | | 1.5 | 1.5 | 1.5 | | |
| Condensate of 20 moles OE in castor oil | 3.1 | 6.5 | 3.0 | 3.0 | 3.2 | 3.0 | 2.9 | 2.9 | | 4.5 |
| Condensate of 30 moles OE in castor oil | | | | | | | | | 3.4 | |
| Solvent: qsp 100% (w/w) | | | | | SOLVESSO 200 | | | | | |
| Density of the CE at 20° C. | 1.247 | 1.242 | 1.114 | 1.113 | 1.272 | 1.283 | 1.150 | 1.136 | 1.140 | 1.292 |

(*) Galoryl EM 514 is the manufacturing trademark of an anionic emulsifier marketed by Applicants.

TESTS IN THE GREENHOUSE

Plants were sown in pots containing garden earth and they were cultivated normally for balanced vegetation. These plants were selected by taking into consideration the respective activity spectra of ioxynil and bromoxynil.

The aqueous emulsions of herbicides were applied by spraying when the plants reached the stage of 2 to 4 leaves, the volume of slurry being 1000 liters per hectare and the doses of each active substance those indicated in tables G and J relating respectively to the products based on bromoxynil and ioxynil, these tables giving also the composition of the emulsifiable concentrates employed.

*Daucus carota*
*Matricaria inodora*
*Papaver rhoeas*
*Raphanus sativus*
*Solanum nigrum*
*Taraxacum dens leonis*
*Veronica agrestis* in the case of ioxynil-based products:
*Amarantus retroflexus*
*Beta vulgaris*
*Brassica oleifera*
*Chenopodium album*
*Daucus carota*
*Galium aparine*
*Papaver rhoeas*

*Raphanus sativus*
*Stellaria media*
*Taraxacum dens leonis*
*Veronica agrestis.*

EXAMPLE 5

This example relates to experiments carried out with products based on bromoxynil esters.

These herbicides were sprayed on plants in pots. The contents of bromoxynil of the concentrated products are given in g/l and the percentages per unit volume required of the concentrated products with respect to water to be able to treat seedlings at 1000 l/ha at the doses studied of 125 to 500 g of bromoxynil/ha are given in the following Table G, in which there are also identified, with reference to Tables E and F, the esters or mixtures of esters used.

Comparison of the averages (qualitative) on the whole plant group shows that the mixtures according to the invention (emulsifiable concentrates n and l), contrarily to branched esters alone of bromoxynil (emulsifiable concentrates s and t), have an effectiveness comparable with that of the linear ester mixtures (emulsifiable concentrates q and r) and particularly with that of concentrate q.

The branched esters alone are not effective at the doses studied.

Comparison of the effectiveness averages on plants resistant to the conventional mixture q shows even more the effectiveness of the mixtures according to the invention and the little interest of the branched esters alone.

EXAMPLE 6

TABLE G

| Identification of emulsifiable concentrate used | Ester or mixture of bromoxynil esters | content of active material (g/l) | % vol. of product in water used for the dose | | |
|---|---|---|---|---|---|
| | | | 125 g/ha bromoxynil | 250 g/ha bromoxynil | 500 g/ha bromoxynil |
| n, Table E | n-heptanoate/n-butyrate/cekanoate | 600 | 0.0208 | 0.0417 | 0.0833 |
| l, Table E | n-heptanoate/n-butyrate/2-ethyl-hexanoate | 600 | 0.0208 | 0.0417 | 0.0833 |
| q, Table F | n-octanoate/n-butyrate | 480 | 0.0260 | 0.0521 | 0 1042 |
| r, Table F | n-heptanoate/n-butyrate | 480 | 0.0260 | 0.0521 | 0.1042 |
| s, Table F | cekanoate | 240 | 0.0521 | 0.1042 | 0.2083 |
| t, Table F | 2-ethyl-hexanoate | 240 | 0.0521 | 0.1042 | 0.2083 |

The observations carried out at the end of the tests resulted in the marks or ratings assembled in Table H.

The averages of the effectiveness ratings (average of two tests) are given per plant and then overall (general average of the ratings recorded for all of the plants) and finally limited to the interesting plants marked with an asterisk in Table H.

This example relates to experiments carried out with products based on ioxynil esters.

These herbicides have also been sprayed on plants in pots. The contents of ioxynil of the concentrated products are given in g/l and the percentages per unit volume necessary of the concentrated products with respect to water to be able to treat seedlings at 1000 l/ha

TABLE H

| | Emulsifiable concentrate based on | | | | | | | | | | | | | | | | | |
|---|---|---|---|---|---|---|---|---|---|---|---|---|---|---|---|---|---|---|
| | bromoxynil n-heptonate/cekanoate n, Table E | | | bromoxynil n-heptanoate/n-butyrate/2-ethyl-hexanoate l, Table E | | | bromoxynil n-octanoate/n-butyrate/ q, Table F | | | bromoxynil n-heptanoate/n-butyrate r, Table F | | | bromoxynil cekanoate s, Table F | | | bromoxynil 2-ethyl-hexanoate t, Table F | | |
| | DOSE OF ACTIVE MATERIAL in grams to the hectare | | | | | | | | | | | | | | | | | |
| Plants tested | 125 | 250 | 500 | 125 | 250 | 500 | 125 | 250 | 500 | 125 | 250 | 500 | 125 | 250 | 500 | 125 | 250 | 500 |
| | Ratings obtained | | | | | | | | | | | | | | | | | |
| *Amarantus retroflexus | 5 | 6 | 8 | 4 | 6 | 8 | 3 | 6 | 7 | 2 | 4 | 7 | 2 | 3 | 4 | 5 | 5 | 5 |
| Brassica oleifera | 9 | 10 | 10 | 10 | 10 | 10 | 10 | 10 | 10 | 9 | 10 | 10 | 9 | 10 | 10 | 0 | 0 | 2 |
| *Daucus carota | 2 | 3 | 10 | 6 | 10 | 10 | 5 | 7 | 10 | 4 | 7 | 9 | 1 | 2 | 3 | 0 | 0 | 0 |
| Matricaria inodora | 8 | 9 | 10 | 9 | 9 | 10 | 10 | 10 | 10 | 7 | 10 | 10 | 2 | 6 | 7 | 1 | 1 | 2 |
| Papaver rhoeas | 3 | 9 | 10 | 10 | 10 | 10 | 9 | 10 | 10 | 10 | 10 | 10 | 7 | 9 | 10 | 0 | 0 | 5 |
| *Raphanus sativus | 5 | 6 | 8 | 8 | 9 | 10 | 4 | 8 | 9 | 5 | 8 | 9 | 2 | 6 | 7 | 0 | 0 | 5 |
| Solanum nigrum | 10 | 10 | 10 | 10 | 10 | 10 | 10 | 10 | 10 | 10 | 10 | 10 | 9 | 10 | 10 | 2 | 4 | 8 |
| Taraxacum dens leonis | 5 | 7 | 10 | 9 | 10 | 10 | 9 | 10 | 10 | 4 | 6 | 8 | 5 | 7 | 7 | 0 | 0 | 0 |
| Veronica agrestis | 6 | 8 | 9 | 8 | 10 | 10 | 9 | 9 | 10 | 9 | 9 | 10 | 7 | 8 | 8 | 0 | 0 | 1 |
| general average | 5.9 | 7.6 | 9.4 | 8.2 | 9.3 | 9.8 | 7.7 | 8.9 | 9.6 | 6.7 | 8.2 | 9.2 | 4.9 | 6.8 | 7.3 | 0.9 | 1.1 | 3.1 |
| average on interesting plants (marked*) | 4.0 | 5.0 | 8.7 | 6.0 | 8.3 | 9.3 | 4.0 | 7.0 | 8.7 | 3.7 | 6.3 | 8.3 | 1.7 | 3.7 | 4.7 | 1.7 | 1.7 | 3.1 |

Examination of Table H permits the following observations to be made.

at the doses studied of 125 to 500 g of ioxynil/ha are given in the following Table J.

TABLE J

| Identification of emulsifiable concentrate used | Ester or mixture of ioxynil esters | content of active material (g/l) | % vol. of product in water used for the dose | | |
|---|---|---|---|---|---|
| | | | 125 g/ha ioxynil | 250 g/ha ioxynil | 500 g/ha ioxynil |
| $p_1$, Table E | n-heptanoate/n-butyrate/cekanoate | 600 | 0.0208 | 0.0417 | 0.0833 |
| m, Table E | n-heptanoate/n-butyrate/2-ethyl-hexanoate | 600 | 0.0208 | 0.0417 | 0.0833 |
| u, Table F | n-octanoate/n-butyrate | 480 | 0.0260 | 0.0521 | 0.1042 |
| v, Table F | n-heptanoate/n-butyrate | 480 | 0.0260 | 0.0521 | 0.1042 |
| w, Table F | cekanoate | 240 | 0.0521 | 0.1042 | 0.2083 |
| x, Table F | 2-ethyl-hexanoate | 240 | 0.0521 | 0.1042 | 0.2083 |

The observations made after the tests resulted in the ratings assembled in Table K.

The averages of the effectiveness ratings (mean of two tests) are given by plant, then overall (general average of the ratings recorded for all of the lastly limited to the interesting plants marked with an asterisk in Table K.

Examination of Table K permits the following observations to be made.

Comparison of the efficiency averages on the plants shows that the mixtures according to the invention (emulsifiable concentrates $p_1$ and m), contrarily to branched esters alone of ioxynil (emulsifiable concentrates w and x), have an efficiency comparable with that of the conventional linear ester mixtures (emulsifiable concentrates u and v).

The branched esters alone are not effective at the doses studied.

Comparison of the effectiveness averages on plants resistant to the conventional mixture u shows even more the effectiveness of the mixtures according to the invention and the little interest of the branched esters alone.

FIELDS TESTS

The field tests were carried out on 10 fields located differently to obtain vegetation conditions very different from one another so as to be able to evaluate the reactions of the plants in various climatic circumstances.

Plots of 15 to 22 m² were sown with winter cereals. Each test was repeated twice and untreated control plots, were provided every two plots. There were applied between the start and full tillering different herbicidal products formulated in emulsifiable concentrates, emulsified in water at the dose of 500 l of liquid per hectare (this dose was intermediate in the group of suitable doses).

Three types of comparative tests followed, namely:

a first type of comparative test (Example 7) in which there were employed two mixtures of ioxynil esters according to the invention, a conventional mixture of ioxynil esters and a single ester of ioxynil, a second type of comparative test (Example 8) in which there were employed a mixture of herbicidal products according to the invention based on ioxynil and herbicidal products according to the invention based on bromoxynil and a mixture of conventional herbicidal products based on ioxynil and conventional herbicidal products based on bromoxynil and a third type of test (Example 9) in which, with mixtures of the second type of test, isoproturon was associated.

TABLE K

| | Emulsifiable concentrate based on | | | | | | | | | | | | | | | | | |
|---|---|---|---|---|---|---|---|---|---|---|---|---|---|---|---|---|---|---|
| | ioxynil n-heptonate/n-butyrate/cekanoate $p_1$, Table E | | | ioxynil n-heptanoate/n-butyrate/2-ethyl-hexanoate m, Table E | | | ioxynil n-octanoate/n-butyrate u, Table F | | | ioxynil n-heptanoate/n-butyrate v, Table F | | | ioxynil cekanoate w, Table F | | | ioxynil 2-ethyl-hexanoate x, Table F | | |
| | DOSE OF ACTIVE MATERIAL in grams to the hectare | | | | | | | | | | | | | | | | | |
| Plants tested | 125 | 250 | 500 | 125 | 250 | 500 | 125 | 250 | 500 | 125 | 250 | 500 | 125 | 250 | 500 | 125 | 250 | 500 |
| | Ratings obtained | | | | | | | | | | | | | | | | | |
| *Amarantus/retroflexus | 6 | 9 | 10 | 5 | 10 | 10 | 4 | 10 | 10 | 5 | 9 | 10 | 1 | 9 | 10 | 0 | 2 | 4 |
| Beta vulgaris | 10 | 10 | 10 | 10 | 10 | 10 | 10 | 10 | 10 | 10 | 10 | 10 | 10 | 10 | 10 | 0 | 3 | 5 |
| Brassica oleifera | 10 | 10 | 10 | 10 | 10 | 10 | 10 | 10 | 10 | 10 | 10 | 10 | 2 | 5 | 10 | 0 | 0 | 0 |
| Chenopodium album | 3 | 4 | 8 | 4 | 9 | 10 | 9 | 10 | 10 | 7 | 10 | 10 | 0 | 7 | 10 | 5 | 5 | 8 |
| Daucus carota | 3 | 9 | 10 | 5 | 10 | 10 | 10 | 10 | 10 | 7 | 10 | 10 | 2 | 2 | 2 | 0 | 1 | 1 |
| *Galium aparine | 2 | 4 | 10 | 7 | 8 | 10 | 5 | 10 | 10 | 6 | 8 | 9 | 2 | 9 | 10 | 0 | 0 | 3 |
| Papaver rhoeas | 3 | 10 | 10 | 8 | 9 | 10 | 10 | 10 | 10 | 7 | 10 | 10 | 0 | 3 | 7 | 2 | 6 | 9 |
| *Raphanus sativus | 7 | 10 | 10 | 6 | 10 | 10 | 7 | 9 | 10 | 1 | 5 | 10 | 2 | 6 | 7 | 1 | 1 | 4 |
| Stellaria media | 9 | 10 | 10 | 6 | 10 | 10 | 8 | 10 | 10 | 6 | 10 | 10 | 1 | 2 | 8 | 0 | 0 | 1 |
| *Taraxacum dens leonis | 9 | 9 | 10 | 6 | 10 | 10 | 6 | 8 | 10 | 9 | 10 | 10 | 2 | 3 | .7 | 0 | 1 | 1 |
| Veronica agrestis | 5 | 10 | 10 | 5 | 10 | 10 | 10 | 10 | 10 | 7 | 10 | 10 | 1 | 3 | 3 | 0 | 0 | 1 |
| general average | 6.1 | 8.6 | 9.8 | 6.5 | 9.6 | 10 | 8.1 | 9.7 | 10 | 6.8 | 9.3 | 9.9 | 2.1 | 5.4 | 7.6 | 0.7 | 1.7 | 3.4 |
| average in interesting plants (marked*) | 6.0 | 8.0 | 10 | 6.0 | 9.5 | 10 | 5.5 | 9.2 | 10 | 5.2 | 8.0 | 9.7 | 1.7 | 6.7 | 8.5 | 0.2 | 1.0 | 3.0 |

In all these tests, the oxynils were esterified either with acids provided according to the invention, or with acids previously used, namely octanoic acid or a mixture of octanoic and butyric acids.

The mixtures of bromoxynil esters alone were not tried in the field since these herbicides employed alone do not present, on the plants subjected to the tests, a sufficient herbicidal spectrum in the cultivation of Fall cereals under French conditions.

The plots were observed about 45 days after treatment. To the extent that the checking of the nature of the adventitious species plants was not ensured and where the latter were present hazardously or in aleatory manner in all of the fields, only the percentage destruction of weeds present in at least two fields of cereals was noted.

EXAMPLE 7

This Example relates to experiments carried out with products based on ioxynil esters.

These herbicides have also been sprayed on fields. The contents of ioxynil of the concentrated products are given in g/l and the percentages by volume necessary of the concentrated products with respect to water to be able to treat the fields at 500 l/ha at the doses studied of 360 to 480 g of ioxynil/ha are given in the following Table L.

TABLE L

| Identification of emulsifiable concentrate used | Ester or mixture of ioxynil esters | content of active material (g/l) | % vol. of product in water used for the dose of 360 g/ha ioxynil | 480 g/ha ioxynil |
|---|---|---|---|---|
| p₁, Table E | n-heptanoate/n-butyrate/cekanoate | 600 | 0.12 | 0.16 |
| m, Table E | n-heptanoate/n-butyrate/2-ethyl-hexanoate | 600 | 0.12 | 0.16 |
| u, Table F | n-octanoate/n-butyrate | 480 | 0.15 | 0.20 |
| y, Table F | n-octanoate | 240 | 0.30 | 0.40 |

The list of plants present in each of the ten fields numbered from 1 to 10 is given in Table M.

TABLE M

| PLANTS | 1 | 2 | 3 | 4 | 5 | 6 | 7 | 8 | 9 | 10 |
|---|---|---|---|---|---|---|---|---|---|---|
| Anthemis cotula | | | | | | | | | | x |
| Aphanes arvensis | | | | | x | | x | | | |
| Arabidopsis thaliana | | | | | x | x | x | | | |
| Capsella bursa-pastoris | | | | x | | | | | | |
| Cerastium glomeratum | | | | | x | | x | | x | |
| Fumaria officinalis | | | | x | | | | | | |
| Galium aparine | | x | x | | | | | | | |
| Juneus bufonius | | | | | | | | x | | |
| Lamium amplexicaule | | | | x | | | | | | |
| Lamium purpureum | | | | | | | | | x | |
| Legousia speculum-veneris | | | | x | | | | | | |
| Matricaria inodora | x | | | | x | x | x | x | | |
| Papaver rhoeas | | | x | x | x | x | | | | |
| Picris setoria | | | | | | | | x | | |
| Polygonum aviculare | | | | | x | | | x | | x |
| Polygonum convolvulus | | | | | | | | | | x |
| Polygonum Spp | | | | | | x | x | x | | |
| Ranunculus sardous | | | | | | | | | x | |
| Raphanus raphanistrum | | | | | | x | | x | | |
| Stellaria media | x | x | x | | | | x | | x | |
| Veronica agrestis | | | | x | | | | | | |
| Veronica hederifolia | | | x | x | x | x | | | | x |
| Veronica persica | | | | | x | | x | | | |
| Viola tricolor | | | | | | | | x | | | x = plant present in the field

The activity results at 45 days (% reaction of the weeds destroyed) are given for each field per plant in Table N, then the efficiency averages are given for each plant and overall for the plants present in at least 2, 3 and 4 fields (2, 3 and 4 replications of each plant) in Table P.

TABLE N

| | | Emulsifiable Concentrate | | | | | | | |
|---|---|---|---|---|---|---|---|---|---|
| | | ioxynil n-heptanoate/ n-butyrate/ cekanoate (p₁, Table E) | | ioxynil n-heptanoate n-butyrate/ 2-ethyl-hexanoate (m, Table E) | | ioxynil n-octanoate/ n-butyrate (u, Table F) | | ioxynil n-octanoate (y, Table F) | |
| | | Dose ioxynil (g/hectare) | | | | | | | |
| PLANT | Field | 360 | 480 | 360 | 480 | 360 | 480 | 360 | 480 |
| | | Ratings obtained | | | | | | | |
| Aphanes arvensis | field 5 | 8 | 8 | 9 | 9 | 10 | 10 | 7 | 8 |
| | field 7 | 9 | 9 | 10 | 10 | 9 | 10 | 8 | 9 |
| | average | 8.5 | 8.5 | 9.5 | 9.5 | 9.5 | 10 | 7.5 | 8.5 |
| Arabidopsis thaliana | field 5 | 10 | 10 | 10 | 10 | 10 | 10 | 10 | 10 |
| | field 6 | 10 | 9 | 10 | 10 | 10 | 10 | 8 | 10 |
| | field 7 | 10 | 10 | 10 | 10 | 10 | 10 | 10 | 10 |
| | average | 10 | 9.6 | 10 | 10 | 10 | 10 | 9.3 | 10 |
| Cerastium glomeratum | field 5 | 10 | 10 | 10 | 10 | 9 | 10 | 10 | 10 |
| | field 7 | 9 | 9 | 8 | 8 | 7 | 9 | 6 | 7 |
| | field 9 | 3 | 3 | 3 | 3 | 3 | 4 | 3 | 3 |
| | average | 7.3 | 7.3 | 7.0 | 7.0 | 6.3 | 7.6 | 6.3 | 6.6 |
| Galium aparine | field 2 | 6 | 2 | 3 | 3 | 2 | 4 | 2 | 2 |
| | field 3 | 3 | 4 | 7 | 5 | 8 | 8 | 2 | 4 |
| | average | 4.5 | 3.0 | 5.0 | 4.0 | 5.0 | 6.0 | 2.0 | 3.0 |
| Matricaria | field 1 | 3 | 3 | 4 | 2 | 2 | 3 | 2 | 2 |

TABLE N-continued

| | | Emulsifiable Concentrate | | | | | | |
|---|---|---|---|---|---|---|---|---|
| | | ioxynil n-heptanoate/ n-butyrate/ cekanoate (p₁, Table E) | | ioxynil n-heptanoate n-butyrate/ 2-ethyl-hexanoate (m, Table E) | | ioxynil n-octanoate/ n-butyrate (u, Table F) | | ioxynil n-octanoate (y, Table F) |
| | | Dose ioxynil (g/hectare) | | | | | | |
| PLANT | Field | 360 | 480 | 360 | 480 | 360 | 480 | 360 | 480 |
| | | Ratings obtained | | | | | | |
| inodora | field 5 | 10 | 10 | 10 | 10 | 10 | 10 | 10 | 10 |
| | field 6 | 10 | 6 | 8 | 6 | 10 | 10 | 10 | 10 |
| | field 7 | 8 | 9 | 10 | 10 | 9 | 10 | 8 | 9 |
| | field 8 | 3 | 4 | 4 | 5 | 7 | 9 | 5 | 6 |
| | average | 6.8 | 6.4 | 7.2 | 6.6 | 7.6 | 8.4 | 7 | 7.4 |
| Papaver rhoeas | field 3 | 10 | 10 | 10 | 10 | 8 | 10 | 2 | 7 |
| | field 4 | 5 | 6 | 3 | 5 | 5 | 6 | 2 | 4 |
| | field 5 | 9 | 9 | 9 | 9 | 10 | 10 | 8 | 10 |
| | field 6 | 10 | 6 | 10 | 8 | 8 | 8 | 5 | 5 |
| | average | 8.5 | 7.7 | 8.0 | 8.0 | 7.7 | 8.5 | 4.5 | 6.5 |
| Polygonum aviculare | field 4 | 5 | 3 | 2 | 4 | 4 | 5 | 6 | 2 |
| | field 8 | 5 | 4 | 5 | 6 | 8 | 8 | 6 | 7 |
| | field 10 | 3 | 4 | 3 | 4 | 3 | 5 | 3 | 3 |
| | average | 4.3 | 3.6 | 3.3 | 4.6 | 5 | 6 | 5 | 4 |
| Polygonum spp | field 5 | 10 | 9 | 8 | 8 | 8 | 9 | 6 | 6 |
| | field 6 | 7 | 3 | 6 | 5 | 5 | 8 | 7 | 6 |
| | field 7 | 8 | 8 | 9 | 9 | 9 | 10 | 10 | 10 |
| | average | 8.3 | 6.6 | 7.6 | 7.3 | 7.3 | 9 | 7.6 | 7.3 |
| Raphanus raphanistrum | field 5 | 9 | 9 | 8 | 9 | 10 | 9 | 9 | 9 |
| | field 7 | 10 | 10 | 10 | 10 | 10 | 10 | 10 | 10 |
| | average | 9.5 | 9.5 | 9.0 | 9.5 | 10 | 9.5 | 9.5 | 9.5 |
| Stellaria media | field 1 | 2 | 2 | 4 | 2 | 2 | 2 | 4 | 2 |
| | field 2 | 3 | 2 | 3 | 3 | 2 | 2 | 2 | 2 |
| | field 3 | 2 | 5 | 8 | 10 | 5 | 5 | 2 | 4 |
| | field 7 | 7 | 8 | 8 | 7 | 6 | 9 | 6 | 5 |
| | field 9 | 3 | 3 | 3 | 3 | 3 | 3 | 3 | 3 |
| | average | 3.4 | 4.0 | 5.2 | 5.0 | 3.6 | 4.2 | 3.4 | 3.2 |
| Veronica hederifolia | field 3 | 2 | 2 | 5 | 3 | 7 | 8 | 2 | 5 |
| | field 4 | 2 | 3 | 2 | 2 | 4 | 6 | 8 | 2 |
| | field 5 | 10 | 10 | 10 | 10 | 10 | 10 | 8 | 10 |
| | field 6 | 5 | 2 | 7 | 4 | 5 | 5 | 2 | 3 |
| | field 10 | 4 | 6 | 4 | 7 | 5 | 7 | 4 | 5 |
| | average | 4.6 | 4.6 | 5.6 | 5.2 | 6.2 | 7.2 | 4.8 | 5.0 |
| Veronica persica | field 4 | 6 | 6 | 4 | 6 | 8 | 7 | 8 | 6 |
| | field 6 | 10 | 8 | 8 | 10 | 10 | 10 | 10 | 10 |
| | average | 8.0 | 7.0 | 6.0 | 8.0 | 9.0 | 8.5 | 9.0 | 8.0 |

TABLE P

| | | Emulsifiable concentrate based on | | | | | | |
|---|---|---|---|---|---|---|---|---|
| | | ioxynil n-heptanoate/ n-butyrate/ cekanoate (p₁, Table E) | | ioxynil n-heptanoate/ n-butyrate/ 2-ethyl-hexanoate (m, Table E) | | ioxynil n-octanoate/ n-butyrate (u, Table F) | | ioxynil n-octanoate (y, Table F) |
| | Nb of fields | Dose of active material (g/ha) | | | | | | |
| PLANT | concerned by the plant | 360 | 480 | 360 | 480 | 360 | 480 | 360 | 480 |
| | | Average ratings | | | | | | |
| Aphanes arvensis | 2 | 8.5 | 8.5 | 9.5 | 9.5 | 9.5 | 10 | 7.5 | 8.5 |
| Arabidopsis thaliana | 3 | 10 | 9.6 | 10 | 10 | 10 | 10 | 9.3 | 10 |
| Cerastium glomeratum | 3 | 7.3 | 7.3 | 7.0 | 7.0 | 6.3 | 7.6 | 6.3 | 6.6 |
| Galium aparine | 2 | 4.5 | 3.0 | 5.0 | 4.0 | 5.0 | 6.0 | 2.0 | 3.0 |
| Matricaria inodora | 5 | 6.8 | 6.4 | 7.2 | 6.6 | 7.6 | 8.4 | 7.0 | 7.4 |
| Papaver rhoeas | 4 | 8.5 | 7.7 | 8.0 | 8.0 | 7.7 | 8.5 | 4.5 | 6.5 |
| Polygonum aviculare | 3 | 4.3 | 3.6 | 3.3 | 4.6 | 5.0 | 6.0 | 5.0 | 4.0 |
| Polygonum spp | 3 | 8.3 | 6.6 | 7.6 | 7.3 | 7.3 | 9.0 | 7.6 | 7.3 |
| Raphanus raphanistrum | 2 | 9.5 | 9.5 | 9.0 | 9.5 | 10 | 9.5 | 9.5 | 9.5 |
| Stellaria media | 5 | 3.4 | 4.0 | 5.2 | 5.0 | 3.6 | 4.2 | 3.6 | 3.2 |
| Veronica hederifolia | 5 | 4.6 | 4.6 | 5.6 | 5.2 | 6.2 | 7.2 | 4.8 | 5.0 |
| Veronica persica | 2 | 8.0 | 7.0 | 6.0 | 8.0 | 9.0 | 8.5 | 9.0 | 8.0 |
| Average activity | | | | | | | | | |

TABLE P-continued

| | | Emulsifiable concentrate based on | | | | | | |
|---|---|---|---|---|---|---|---|---|
| | | ioxynil n-heptanoate/ n-butyrate/ cekanoate (p₁, Table E) | | ioxynil n-heptanoate/ n-butyrate/ 2-ethyl-hexanoate (m, Table E) | | ioxynil n-octanoate/ n-butyrate (u, Table F) | | ioxynil n-octanoate (y, Table F) |
| | Nb of fields | Dose of active material (g/ha) | | | | | | |
| PLANT | concerned by the plant | 360 | 480 | 360 | 480 | 360 | 480 | 360 | 480 |
| | | Average ratings | | | | | | | |
| (plants present in 2 fields and more) | | 7.0 | 6.5 | 7.0 | 7.1 | 7.2 | 7.9 | 6.3 | 6.6 |
| (plants present in 3 fields and more) | | 6.7 | 6.2 | 6.7 | 6.7 | 6.7 | 7.6 | 6.0 | 6.2 |
| (plants present in 4 fields and more) | | 5.8 | 5.7 | 6.5 | 6.2 | 6.3 | 7.1 | 5.0 | 5.5 |

On examining Tables N and P, the following observations can be made.

The mixtures $p_1$ and m according to the invention behave, from the point of view of herbicidal effectiveness on weeds of winter cereals, in the fields, intermediately between the two known herbicides u and y. They can hence be considered as effectively herbicidal at the doses used in the prior art.

It is to be noted that the winter cereals have not been affected by any of the herbicides at any of the doses tried.

EXAMPLE 8

Mixtures of ioxynil esters and bromoxynil esters

The herbicides based on ioxynil and bromoxynil in the form of esters (see Table R) were sprayed on fields. The contents of products concentrated in ioxynil and bromoxynil are given in g/l and the percentages by volume necessary of the concentrated products with respect to water to be able to treat the fields at 500 l/ha at the doses studied of 180 g of ioxynil plus 180 g of bromoxynil and 240 g of ioxynil plus 240 g of bromoxynil/ha are given in the following Table R.

TABLE R

| Identification of the emulsifiable concentrates used | Active substances | Content of active substances (g/l) | % vol. of product in water for the dose of | |
|---|---|---|---|---|
| | | | 180 g/ha bromoxynil + 180 g/ha ioxynil | 240 g/ha bromoxynil + 240 g/ha ioxynil |
| z, Table F | ioxynil n-octanoate/n-butyrate bromoxynil n-octanoate/n-butyrate | 480 | 0.15 | 0.20 |
| p₁, Table E | ioxynil n-heptanoate/n-butyrate/ cekanoate | 600 | 0.06 | 0.08 |
| n, Table E | bromoxynil n-heptanoate/n-butyrate/ cekanoate | 600 | 0.06 | 0.08 |

The list of plants present in each of the ten fields treated is given in Table S.

TABLE S

| | FIELDS | | | | | | | | | |
|---|---|---|---|---|---|---|---|---|---|---|
| PLANTS | 1 | 2 | 3 | 4 | 5 | 6 | 7 | 8 | 9 | 10 |
| Anthemis cotula | | | | x | | | | | | |
| Aphanes arvensis | | | | | x | | x | | | |
| Arabidopsis thaliana | | | | | | x | x | | | |
| Capsella bursa-pastoris | | | | x | | | | | | |
| Cardamine hirsuta | | | | | | | | | x | |
| Cerastium glomeratum | | | | | x | | x | x | x | |
| Fumaria officinalis | | | | | x | | | | | |
| Galium aparine | | | | x | | | | | | |
| Juneus bufonius | | | | | | | | x | | |
| Lamium purpureum | | | | | | | | | x | |
| Legousia speculum-veneris | | | | | x | | | | | |
| Matricaria chamomilla | | | | | | | | x | | |
| Matricaria inodora | x | | | | x | x | x | | | |
| Picris setoria | | | | | | | | x | | |
| Polygonum aviculare | | | | | x | | | x | | x |
| Polygonum convolvulus | | | | | | | | | | x |
| Polygonum Spp | | | | x | x | x | | | | |
| Ranunculus sardous | | | | | | | | | x | |
| Stellaria media | x | x | x | | | | x | | x | |
| Veronica agrestis | | | | x | | | | | | |
| Veronica hederifolia | | x | | | | x | | | | x |
| Veronica persica | | | x | x | x | | | | | |
| Viola tricolor | | x | | | | | | x | | | x = plant present in the field

The results of effectiveness at 45 days (% reaction of weeds) are given for each field and by plant in Table T, then the average activities are given for each plant and overall for the plants present in at least 2, 3 and 4 fields (2, 3 and 4 replications of each plant) in Table U.

TABLE T

| | | Emulsifiable Concentrate | | | |
|---|---|---|---|---|---|
| | | . ioxynil . bromoxynil n-octanoate/n-butyrate 8, Table F | | . ioxynil . bromoxynil n-heptanoate/n-butyrate/cekanoate p₁ and n, Table E | |
| | | Oxynil Dose (g/ha) | | | |
| PLANT | field | 180 + 180 | 240 + 240 | 180 + 180 | 240 + 240 |
| | | | | Ratings | |
| *Aphanes* | field 5 | 9 | 10 | 10 | 9 |
| *arvensis* | field 7 | 10 | 10 | 10 | 10 |
| | average | 9.5 | 10 | 10 | 9.5 |
| *Arabidopsis* | field 6 | 8 | 10 | 10 | 10 |
| *thaliana* | field 7 | 9 | 8 | 10 | 10 |
| | average | 8.5 | 9.0 | 10 | 10 |
| *Cerastium* | field 5 | 10 | 10 | 10 | 10 |
| *glomeratum* | field 7 | 4 | 5 | 8 | 7 |
| | field 8 | 5 | 5 | 5 | 5 |
| | field 9 | 3 | 3 | 3 | 3 |
| | average | 5.5 | 5.7 | 6.5 | 6.2 |
| *Matricaria* | field 1 | 4 | 5 | 2 | 6 |
| *inodora* | field 5 | 10 | 10 | 10 | 10 |
| | field 6 | 10 | 10 | 10 | 10 |
| | field 7 | 10 | 10 | 9 | 10 | 10 |
| | average | 8.5 | 8.5 | 8.0 | 9.0 |
| *Polygonum* | field 4 | 6 | 8 | 7 | 8 |
| *aviculare* | field 8 | 8 | 8 | 7 | 10 |
| | field 10 | 5 | 6 | 6 | 7 |
| | average | 6.3 | 7.3 | 6.6 | 8.3 |
| Polygonum | field 5 | 10 | 10 | 10 | 10 |
| Spp | field 6 | 4 | 4 | 5 | 7 |
| | field 7 | 9 | 10 | 10 | 10 |
| | average | 7.6 | 8.0 | 8.3 | 9.0 |
| *Stellaria* | field 1 | 2 | 2 | 2 | 2 |
| *media* | field 2 | 2 | 2 | 2 | 2 |
| | field 3 | 8 | 5 | 7 | 6 |
| | field 7 | 5 | 4 | 7 | 8 |
| | field 9 | 3 | 4 | 4 | 4 |
| | average | 4.0 | 3.4 | 4.4 | 4.4 |
| *Veronica* | field 3 | 4 | 5 | 3 | 4 |
| *hederifolia* | field 6 | 4 | 3 | 3 | 4 |
| | field 10 | 3 | 4 | 4 | 7 |
| | average | 3.6 | 4.0 | 3.3 | 5.0 |
| *Veronica* | field 4 | 6 | 10 | 7 | 8 |
| *persica* | field 5 | 10 | 10 | 10 | 10 |
| | field 6 | 9 | 9 | 10 | 7 |
| | average | 8.3 | 9.6 | 9.0 | 8.3 |
| *Viola* | field 3 | 10 | 5 | 10 | 10 |
| *tricolor* | field 8 | 3 | 4 | 5 | 6 |
| | average | 6.5 | 4.5 | 7.5 | 8.0 |

TABLE U

| | | Emulsifiable Concentrates | | | |
|---|---|---|---|---|---|
| | | . ioxynil . bromoxynil n-octanoate/n-butyrate z, Table F | | . ioxynil . bromoxynil n-heptanoate/n-butyrate cekanoate p₁ and n, Table E | |
| | | Dose of active material (g/hectare) | | | |
| PLANT | Number of fields involved by the plant | 180 + 180 | 240 + 240 | 180 + 180 | 240 + 240 |
| | | | | Average of the ratings | |
| *Aphanes arvensis* | 2 | 9.5 | 10 | 10 | 9.5 |
| *Arabidopsis thaliana* | 2 | 8.5 | 9.0 | 10 | 10 |
| *Cerastium glomeratum* | 4 | 5.5 | 5.7 | 6.5 | 6.2 |
| *Matricaria inodora* | 4 | 8.5 | 8.5 | 8.0 | 9.0 |
| *Polygonum aviculare* | 3 | 6.3 | 7.3 | 6.6 | 8.3 |
| Polygonum Spp | 3 | 7.6 | 8.0 | 8.3 | 9.0 |
| *Stellaria media* | 5 | 4.0 | 3.4 | 4.4 | 4.4 |
| *Veronica hederifolia* | 3 | 3.6 | 4.0 | 3.3 | 5.0 |
| *Veronica* | 3 | 8.3 | 9.6 | 9.0 | 8.3 |

TABLE U-continued

| | | Emulsifiable Concentrates | | | |
|---|---|---|---|---|---|
| | | . ioxynil . bromoxynil n-octanoate/n-butyrate z, Table F | | . ioxynil . bromoxynil n-heptanoate/n-butyrate cekanoate $p_1$ and n, Table E | |
| | | Dose of active material (g/hectare) | | | |
| PLANT | Number of fields involved by the plant | 180 + 180 | 240 + 240 | 180 + 180 | 240 + 240 |
| | | Average of the ratings | | | |
| persica | | | | | |
| Viola tricolor | 2 | 6.5 | 4.5 | 7.5 | 8.0 |
| Average activity | | | | | |
| (plants present in 2 fields or more) | | 6.8 | 7.0 | 7.4 | 7.8 |
| (plants present in 3 fields or more) | | 6.3 | 6.6 | 6.8 | 7.2 |
| (plants present in 4 fields or more) | | 6.0 | 5.9 | 6.3 | 6.5 |

The mixtures according to the invention ($p_1$ and n, Table E) behaves, from the point of herbicidal effectiveness on weeds of winter cereals, in the fields, in a manner comparable with the known mixture (z, Table F), the differences noted being even to the advantage of the first.

The mixture according to the invention may be considered as effectively herbicidal at the doses used in the prior art.

It is to be noted that winter cereals were not affected by any of the herbicides at any of the doses tested.

EXAMPLE 9

Mixtures of ioxynil esters and bromoxynil esters in association with isoproturon Herbicides based on ioxynil and bromoxynil in the form of esters in admixture with an aqueous suspension of isoproturon (see Table V) were sprayed onto fields. The contents of the products concentrated in ioxynil and bromoxynil are given in g/l and the percentages by volume necessary of the concentrated products with respect to water to be able to treat the fields at 500 l/ha at the doses studied of 180 g of ioxynil plus 180 g of bromoxynil and 240 of ioxynil plus 240 g of bromoxynil/ha are given in said Table V. The isoproturon used was in the form of an aqueous suspension marketed by Ciba Geigy under the name Selfsuspendable Ofal 440. It titrates at 440 g/l. The dose introduced remained constant at 1320 g/ha. This concentrated suspension is also taken up in Table V.

TABLE V

| Identification of the emulsifiable concentrates used | Active substances | Content of active substance (g/l) | % vol. of product in water for the dose of | |
|---|---|---|---|---|
| | | | 180 g/ha bromoxynil + 180 g/ha ioxynil | 240 g/ha bromoxynil + 240 g/ha ioxynil |
| z, Table F | ioxynil n-octanoate/n-butyrate bromoxynil n-octanoate/n-butyrate | 480 | 0.15 | 0.20 |
| + isoproturon | Selfsuspendable Ofal 440 | 440 | 0.6 | 0.6 |
| $p_1$ and n, Table E | ioxynil n-heptanoate/n-butyrate/ cekanoate bromoxynil n-heptanoate/n-butyrate/ cekanoate | 600 600 | 0.06 0.06 | 0.08 0.08 |
| + isoproturon | Selfsuspendable Ofal 440 | 440 | 0.6 | 0.6 |

The list of plants present in each field is given in Table W.

TABLE W

| | FIELDS | | | | | | | |
|---|---|---|---|---|---|---|---|---|
| PLANTS | 1 | 2 | 3 | 4 | 5 | 6 | 7 | 8 |
| Aphanes arvensis | | x | x | | x | | | |
| Galium aparine | x | x | | | | | | |
| Lamium amplexicaule | | x | | | | | | |
| Lamium purpureum | | x | | | | | x | |
| Polygonum Spp | | | | x | x | | | x |
| Raphanus raphanistrum | | | x | | x | | | |
| Stellaria media | | x | | x | x | x | x | |
| Veronica hederifolia | x | x | x | x | | | | x |
| Veronica persica | x | x | x | x | | | x | |
| Viola tricolor | x | | | x | | x | | |

The effectiveness results at 45 days (% reaction of the weeds) are given for each field and per plant in Table Y, then the averages of the activity are given for each plant and overall for the plants present in at least 2, 3 and 4 fields (2, 3 and 4 replications of each plant) in Table Z.

TABLE Y

| | | Concentrates | | | |
|---|---|---|---|---|---|
| | | ioxynil bromoxynil n-octanoate/n-butyrate (+ isoproturon) z, Table F + isoproturon | | ioxynil bromoxynil n-heptanoate/n-butyrate/cekanoate (+ isoproturon) $p_1$ and n, Table E + isoproturon | |
| | | Dose of active material (g/hectare) | | | |
| PLANT | field | 180 + 180 (+1320) | 240 + 240 (+1320) | 180 + 180 (+1320) | 240 + 240 (+1320) |
| | | Ratings | | | |
| Aphanes arvensis | field 2 | 4 | 8 | 5 | 6 |
| | field 3 | 10 | 10 | 10 | 10 |
| | field 5 | 10 | 10 | 10 | 10 |
| | average | 8.0 | 9.3 | 8.3 | 8.6 |
| Galium aparine | field 1 | 8 | 8 | 8 | 8 |
| | field 2 | 4 | 4 | 2 | 3 |
| | average | 6.0 | 6.0 | 5.0 | 5.5 |
| Lamium purpureum | field 2 | 4 | 5 | 3 | 5 |
| | field 7 | 5 | 6 | 8 | 8 |
| | average | 4.5 | 5.5 | 5.5 | 6.5 |
| Polygonum Spp | field 4 | 9 | 8 | 7 | 9 |
| | field 5 | 10 | 10 | 10 | 10 |
| | field 8 | 9 | 8 | 9 | 9 |
| | average | 9.3 | 8.6 | 8.6 | 9.3 |
| Raphanus raphanistrum | field 3 | 10 | 10 | 10 | 10 |
| | field 5 | 10 | 10 | 10 | 10 |
| | average | 10 | 10 | 10 | 10 |
| Stellaria media | field 2 | 2 | 3 | 3 | 6 |
| | field 3 | 10 | 10 | 10 | 10 |
| | field 4 | 10 | 10 | 10 | 10 |
| | field 5 | 10 | 10 | 10 | 10 |
| | field 7 | 7 | 7 | 9 | 9 |
| | average | 7.8 | 8.0 | 8.4 | 9.0 |
| Veronica hederifolia | field 1 | 7 | 5 | 7 | 6 |
| | field 2 | 4 | 8 | 3 | 5 |
| | field 3 | 10 | 10 | 10 | 10 |
| | field 4 | 4 | 4 | 6 | 5 |
| | field 8 | 3 | 3 | 3 | 4 |
| | average | 5.6 | 6.0 | 5.8 | 6.0 |
| Veronica persica | field 1 | 5 | 8 | 8 | 7 |
| | field 2 | 7 | 7 | 8 | 10 |
| | field 3 | 10 | 10 | 10 | 10 |
| | field 4 | 10 | 9 | 10 | 10 |
| | field 7 | 9 | 9 | 8 | 8 |
| | average | 8.2 | 8.6 | 8.8 | 9.0 |
| Viola tricolor | field 1 | 7 | 10 | 10 | 10 |
| | field 4 | 10 | 8 | 10 | 10 |
| | field 6 | 6 | 7 | 8 | 9 |
| | average | 7.6 | 8.3 | 9.3 | 9.6 |

TABLE Z

| | | Concentrates | | | |
|---|---|---|---|---|---|
| | | ioxynil bromoxynil n-octanoate/n-butyrate (+ isoproturon) z, Table F + isoproturon | | ioxynil bromoxynil n-heptanoate/n-butyrate/cekanoate (+ isoproturon) $p_1$ and n, Table E + isoproturon | |
| | | Dose of active material (g/hectare) | | | |
| PLANT | Number of fields involved by the Plant | 180 + 180 (+1320) | 240 + 240 (+1320) | 180 + 180 (+1320) | 240 + 240 (+1320) |
| | | Average of the ratings | | | |
| Aphanes arvensis | 3 | 8.0 | 9.3 | 8.3 | 8.6 |
| Galium aparine | 2 | 6.0 | 6.0 | 5.0 | 5.5 |
| Lamium purpureum | 2 | 4.5 | 5.5 | 5.5 | 6.5 |
| Polygonum Spp | 3 | 9.3 | 8.6 | 8.6 | 9.3 |
| Raphanus raphanistrum | 2 | 10 | 10 | 10 | 10 |
| Stellaria media | 5 | 7.8 | 8.0 | 8.4 | 9.0 |
| Veronica hederifolia | 5 | 5.6 | 6.0 | 5.8 | 6.0 |
| Veronica persica | 5 | 8.2 | 8.6 | 8.8 | 9.0 |
| Viola tricolor | 3 | 7.6 | 8.3 | 9.3 | 9.6 |
| Average activity | | | | | |
| (plants present in 2 fields or more) | | 7.4 | 7.8 | 7.7 | 8.2 |
| (plants present in 3 fields or more) | | 7.8 | 8.1 | 8.2 | 8.6 |

TABLE Z-continued

| | | Concentrates | | | |
|---|---|---|---|---|---|
| | | ioxynil bromoxynil n-octanoate/n-butyrate (+ isoproturon) z, Table F + isoproturon | | ioxynil bromoxynil n-heptanoate/n-butyrate/cekanoate (+ isoproturon) $p_1$ and n, Table E + isoproturon | |
| | | Dose of active material (g/hectare) | | | |
| PLANT | Number of fields involved by the Plant | 180 + 180 (+1320) | 240 + 240 (+1320) | 180 + 180 (+1320) | 240 + 240 (+1320) |
| | | Average of the ratings | | | |
| (plants present in 4 fields or more) | | 7.2 | 7.5 | 7.7 | 8.0 |

The mixture according to the invention associated with isoproturon, behaves, from the point of view of herbicidal effectiveness on weeds of winter cereals, in the field, in a manner comparable with the known mixture (z, Table F+isoproturon), the differences noted being even to the advantage of the mixture according to the invention, which can be considered as effectively herbicidal at the doses used in the prior art.

EXAMPLE 10

Trials, in the field, on maize were carried out at 12 different sites so as to obtain vegetation conditions very different from one another to be able to evaluate the reactions of the plants under various climatic conditions and on different varieties.

On the same site, the applications were carried out at two vegetative stages of the maize, one early at the 2/4 leaf stage, the other late at the 4/8 leaf stage, which is a vegetative state corresponding to the usual range of use of this type of product.

The treatments on plots of 15 to 22 m² were carried out during June. Each treatment was repeated twice.

Untreated control plots were included in the experimental arrangement every pair of plots treated. In each field different herbicidal compositions were applied, formulated as an emulsifiable concentrate, emulsified in water at the dose of 500 l of slurry per hectare (an intermediate dose in the set of suitable doses).

By way of comparison, there was also applied under the same conditions a commercial product as a reference, sold for this use. It was a concentrated aqueous suspension containing 250 g of bromoxynil in phenol form.

There were employed an emulsifiable mixture of esters according to the invention containing octanoate, butyrate and 2-ethyl-hexanoate of bromoxynil (mixture $p_2$ of Table E), an emulsifiable concentrate containing only bromoxynil octanoate in the proportion of 240 g/l and for comparison an aqueous suspension of unesterified bromoxynil.

The product based on bromoxynil phenol, denoted below by "Product α" had the following composition:
Bromoxynil: 250 g/l

| Inert agents in % | |
|---|---|
| Propyleneglycol | 9% |
| Galoryl MT 41* | 0.5% |
| Soprophor FL** | 2% |
| Heteropolysaccharide | 0.3% |
| Preservative | 0.1% |
| Water q.s.p. | 100% |
| (density at 20° C. = 1160) | |

*Galoryl MT 41 is a wetting agent of the non ionic type marketed by Applicants
**Soprophor FL is a dispersing wetting agent of the anionic type marketed by RHONE-POULENC.

The emulsifiable concentrate, called below "Product β", containing bromoxynil octanoate, contains:
bromoxynil in n-octanoate form: 240 g/l
the following inert agents (in %):
  Galoryl EM 4039 5.25%
  Condensate of 20 moles of ethylene oxide on castor oil 4.75%
  Solvesso 200 q.s.p. 100% (density at 20° C.=1119)

Simultaneously, in this test, there was measured the effectiveness of the herbicidal products in the preceding examples (see particularly the ratings given above) and their phytotoxicity on maize according to the following scale:

| mark "n" | phytotoxicity | comments |
|---|---|---|
| 0 < n < 1 | nil | good |
| 1 ≦ n < 2 | very low | good |
| 2 ≦ n < 3 | low | acceptable |
| 3 ≦ n < 4 | moderate | unacceptable |
| 4 ≦ n < 5 | fairly high | " |
| 5 ≦ n < 6 | high | " |
| 6 ≦ n < 7 | very high | " |
| 7 to 10 | very high | " |

The percentage by volume necessary for the concentrated products with respect to water to be able to treat fields at 500 l/ha at the doses studied, are given in the following Table AA:

TABLE AA

| Identification of the concentrate | Compound based on bromoxynil | Content of active material (g/l) | % by vol. of product formulated in water for the dose of: | | |
|---|---|---|---|---|---|
| | | | 360 g/ha bromoxynil | 480 g/ha bromoxynil | 600 g/ha bromoxynil |
| Product α | Non-esterified bromoxynil | 250 | | | 0.48 |
| Product β | bromoxynil n-octanoate | 240 | 0.30 | 0.40 | |
| $p_2$, table E | bromoxynil n-octanoate/ n-butyrate/ 2-ethyl-hexanoate | 600 | 0.12 | 0.16 | |

The results of effectiveness at 25 days (percentage reaction of weeds destroyed) are given as the average per plant then overall for all of the plants present in the following Table BB.

The selectivity results with respect to maize at 25 days evaluated on the above ratings scale are given overall also in Table BB.

There was employed an emulsifiable mixture of esters according to the invention containing n-heptanoate, butyrate and cekanoate of bromoxynil (mixture n, Table

TABLE BB

| | | Concentrate based on | | | |
|---|---|---|---|---|---|
| | | Bromoxynil | Bromoxynil n-octanoate | Bromoxynil n-octanoate n-butyrate 2-ethyl-hexanoate | |
| | | Bromoxynil dose (g/ha) | | | |
| PLANTS | Nb of sites concerned by the plant | 600 | 360 | 480 | 360 | 480 |
| | | Average rating | | | |
| *Amaranthus retroflexus* | 4 | 7.7 | 8.5 | 9.6 | 7.4 | 7.7 |
| *Chenopodium album* | 12 | 9.9 | 9.7 | 9.9 | 9.5 | 9.7 |
| *Senecio vulgaris* | 4 | 10 | 9.6 | 10 | 9.2 | 10 |
| *Solanum nigrum* | 12 | 8.4 | 8.7 | 8.8 | 8 | 9.2 |
| Average activity over all of the sites | | 9 | 9.1 | 9.6 | 8.5 | 9.2 |
| Phytotoxicity (average/10) | | 0.4 | 1 | 1.6 | 0.2 | 1 |
| % sites with marginal phytotoxicity (percentage of sites of which the phytotoxicity rating is ≧ 3) | | 8 | 17 | 29 | 0 | 8 |

The mixture according to the invention behaves, from the point of view of herbicidal effectiveness on weeds of maize in the field, in a manner comparable with unesterified bromoxynil and very slightly less well than bromoxynil octanoate. The latter product, however, does not offer a sufficient guarantee as to inocuity on the maize, in comparison with the formulation based on bromoxynil, taken as a reference.

In this respect, the mixture according to the inventon possesses the same quality as the reference product.

The advantage of the mixture according to the invention with respect to the reference mixture is its dose of utilization which can reasonably be situated at 360 g of bromoxynil per hectare against 600 g per hectare of unesterified bromoxynil. The interest resides at the level of a substantial reduction in the cost of the treatment.

EXAMPLE 11

Test on tender winter wheat

Trials, in the field, on tender winter wheat have been conducted at 10 different sites so as to obtain vegetation conditions very varied from one another to be able to evaluate the reactions of the plants in various conditions of climate and cultivation.

Plots of 15 to 22 m² were sown with various wheat varieties during November. The treatments were carried out during March at the 2-3 leaf stage. Untreated control plots were included every pair of plots treated.

Different herbicidal compositions were applied, formulated as an emulsifiable concentrate, emulsified in water at the dose of 500 l of slurry per hectare (intermediate dose in the group of suitable doses).

E), n-heptanoate, butyrate and cekanoate of ioxynil (mixture p₁, Table E), an emulsifiable concentrate containing 240 g/l of bromoxynil in the form of n-octanoate and of butyrate and 240 g/l of ioxynil in the form of n-octanoate and of butyrate (mixture z, Table F), an emulsifiable concentrate containing 240 g/l of bromoxynil and 240 g/l of ioxynil but this time in the form of n-heptanoate and of butyrate.

The composition of the latter concentrate is given below.

| Proportions of oxynil esters (% moles) | |
|---|---|
| Bromoxynil n-heptanoate | 28 |
| Ioxynil n-heptanoate | 33 |
| Bromoxynil n-butyrate | 22 |
| Ioxynil n-butyrate | 17 |
| Content of active material in the emulsifiable concentrate (in g/l) | 480 |
| Proportions of emulsifiers in the emulsifiable concentrate in % | |
| Galoryl EM 4039 | 5% |
| Condensate of 20 moles of OE on castor oil | 5% |
| Solvent q.s.p. 100% (w/w) | Solvesso 200 |
| (density of the emulsifiable concentrate at 20° C. = 1.265). | |

The effectiveness of the herbicidal compositions was measured as in the preceding examples (see definition of the ratings given above).

The percentages by volume necessary for the concentrated products with respect to water to be able to treat fields at 500 l/ha at the doses studied are given in the following Table CC:

TABLE CC

| | | | % by volume of product formulated in water for the dose of: | |
|---|---|---|---|---|
| Identification of the concentrate used | Compound | Content of active material (g/l) | 180 g/ha bromoxynil + 180 g/ha ioxynil | 240 g/ha bromoxynil + 240 g/ha ioxynil |
| n, table E + p₁, table E | Bromoxynil (n-heptanoate butyrate cekanoate) | 600 | 0.06 + | 0.08 + |
| | Ioxynil (n-heptanoate butyrate cekanoate) | 600 | 0.06 | 0.08 |
| z, table F | Ioxynil and bromoxynil (n-octanoate butyrate) | 480 | 0.15 | 0.2 |
| | Ioxynil and | 480 | 0.15 | 0.2 |

TABLE CC-continued

| Identification of the concentrate used | Compound | Content of active material (g/l) | % by volume of product formulated in water for the dose of: | |
|---|---|---|---|---|
| | | | 180 g/ha bromoxynil + 180 g/ha ioxynil | 240 g/ha bromoxynil + 240 g/ha ioxynil |
| | bromoxynil (n-heptanoate butyrate) | | | |

The results of effectiveness at 45 days (percentage of reaction of the weeds destroyed) are given on the average per plant then overall for all of the plants present, in the following Table DD.

TABLE DD

| | | Compound | | | | | |
|---|---|---|---|---|---|---|---|
| | | Ioxynil/bromoxynil n-octanoate n-butyrate | | Ioxynil/bromoxynil n-heptanoate n-butyrate | | Ioxynil/bromoxynil n-heptanoate n-butyrate cekanoate | |
| | | Dose: g/ha | | | | | |
| | | bromoxynil | | | | | |
| | | 180 | 240 | 180 | 240 | 180 | 240 |
| | | ioxynil | | | | | |
| PLANT | Nb fields concerned by the plants | 180 | 240 | 180 | 240 | 180 | 240 |
| | | Average ratings | | | | | |
| *Aphanes arvensis* | 4 | 9 | 9 | 9 | 9 | 9 | 9 |
| *Arabidopsis thaliana* | 6 | 9 | 9 | 9 | 9 | 9 | 9 |
| *Cerastium glomeratum* | 8 | 6.7 | 6.8 | 6.8 | 7.4 | 7.2 | 7.2 |
| *Matricaria inodora* | 8 | 8.2 | 8.3 | 8 | 8.2 | 8 | 8.6 |
| *Papaver Rhoeas* | 6 | 9 | 8.5 | 8.7 | 9 | 8.7 | 9 |
| *Polygonum aviculare* | 6 | 7.5 | 8.3 | 7.5 | 8.6 | 7.6 | 8.6 |
| *Polygonum convolvulus* | 2 | 7 | 8 | 8 | 8 | 7 | 9 |
| Polygonum SPP | 6 | 8 | 8 | 7.9 | 7.9 | 8.3 | 8.6 |
| *Stellaria media* | 10 | 6 | 5.7 | 6.3 | 6.5 | 5.5 | 6.5 |
| *Veronica hederifolia* | 8 | 6.6 | 6.7 | 6.8 | 7.4 | 5.4 | 6.2 |
| *Veronica persica* | 6 | 6.8 | 9 | 9 | 9 | 8.6 | 8.6 |
| Veronica tricolor | 4 | 7.2 | 6.2 | 6.2 | 6.7 | 7.7 | 9 |
| Average activity | | 7.6 | 7.8 | 7.7 | 8 | 7.6 | 8.2 |

The mixture according to the invention behaves, from the point of view of herbicidal activity on weeds of wheat, in the field, in a manner comparable with the mixture n-octanoate and n-butyrate of bromoxynil and of ioxynil, on the one hand, and with the mixture n-heptanoate and n-butyrate of bromoxynil and ioxynil, on the other hand.

It is to be noted that winter cereals have not been affected by any of the herbicides at any of the doses tested.

We claim:

1. A herbicidal composition comprising a mixture of one or more linear acid esters and one or more branched acid esters of bromoxynil and/or a mixture of one or more linear acid esters and one or more branched acid esters of ioxynil, wherein the linear acids are selected from the group consisting of n-heptanoic and n-octanoic acids associated with n-butyric acid and the branched acids are selected from the group consisting of 2-ethyl-hexanoic acid and the branched mixture known as cekanoic acid, and wherein the proportion of bromoxynil linear acid esters in their mixture with the bromoxynil branched acid esters is from 20 to 90% molar and the proportion of ioxynil linear acid esters in their mixture with the ioxynil branched acids esters is from 30–95% molar, the proportion of branched acid esters in each of both mixtures representing the complement to 100% molar.

2. A herbicidal composition according to claim 1, wherein the proportion of bromoxynil linear esters in their mixture with the bromoxynil branched esters is from 30 to 80% molar.

3. A herbicidal composition according to claim 1, wherein the proportion of ioxynil linear esters in their mixture with the ioxynil branched esters is from 40 to 85% molar.

4. A herbicidal composition according to claim 1, wherein the proportion of bromoxynil linear esters in their mixture with the bromoxynil branched esters is from 30 to 80% molar and wherein the proportion of ioxynil linear esters in their mixture with the ioxynil branched esters is from 40 to 85% molar, the proportion of branched acid esters in each of both mixtures representing the complement to 100% molar.

5. A herbicidal composition according to claim 1, wherein the linear acids are n-heptanoic acid or n-octanoic acid associated with n-butyric acid and wherein the branched acid is 2-ethyl-hexanoic acid.

6. A herbicidal composition according to claim 1, wherein the linear acids are n-heptanoic acid or n-octanoic acid associated with n-butyric acid and wherein the branched acid is cekanoic acid.

7. A herbicidal composition according to claim 1, having a concentration of 100 to 900 g of bromoxynil equivalent and from 100 to 900 g of ioxynil equivalent per liter.

8. A herbicidal composition according to claim 1, wherein the concentration in bromoxynil and/or ioxynil equivalent is comprised between about 600 g/l and about 900 g/l.

9. A herbicidal composition according to claim 1, further comprising one or several solvents selected from among mineral oils with a high content of aromatic substances.

10. A herbicidal composition according to claim 1, further comprising one or several solvents selected from among mineral oils having a content by weight of aromatic substances of at least 70% and a flash point above 50° C.

11. A herbicidal composition according to claim 1, further comprising one or several surfactants which are present in the proportion of 0.1 to 20% by weight and which are selected from the group consisting of products based on ethylene oxide condensates with propylene oxide, with alkylphenols, with polyarylphenols, with vegetable oils saponified or not, or with straight or branched alcohols; anhydrosorbitol carboxylic esters; alkali, alkaline-earth or ammonium salts of sulphuric esters; and sulfonic derivatives with high molecular weight.

12. A herbicidal composition according to claim 1, further comprising one or several surfactants which are present in the proportion of 0.1 to 20% by weight and which are selected from the group consisting of products based on ethylene oxide condensates with nonyl- or octylphenols.

13. A herbicidal composition according to claim 1, further comprising one or several surfactants which are present in the proportion of 0.1 to 20% by weight and which are selected from the group consisting of products based on ethylene oxide condensates with lauric alcohol.

14. A herbicidal composition according to claim 1, further comprising one or several surfactants which are present in the proportion of 0.1 to 20% by weight and which consist of polyethoxylated anhydrosorbitol carboxylic esters.

15. A herbicidal composition according to claim 1, further comprising one or several surfactants which are present in the proportion of 0.1 to 20% by weight and which consist of lignosulphonates or sodium and calcium alkylbenzenesulphonates.

16. A method of destroying adventitious plant species comprising selecting a spraying fluid applicable to the soil, obtained by dilution or emulsion in water of an amount of a herbicidal composition according to claim 1, such that the spraying fluid contains from 0.05 to 5% weight/volume of a mixture of linear and branched esters of bromoxynil and/or of ioxynil and applying the said spraying fluid to the soil at a dose of 50 g to 1 kg/ha of bromoxynil and/or ioxynil equivalent.

* * * * *